United States Patent [19]

Schleicher et al.

[11] Patent Number: 5,760,211
[45] Date of Patent: Jun. 2, 1998

[54] METHOD OF MANUFACTURING CELLULOSE SOLUTIONS IN AQUEOUS AMINO OXIDE

[75] Inventors: Harry Schleicher, Teltow; Peter Weigel, Kleinmachnow; Hendrik Wetzel, Hunstetten, all of Germany

[73] Assignee: Fraunhofer-Gesellschaft Zur Forderung Der Angewandten Forschung E.V., Germany

[21] Appl. No.: 891,512

[22] Filed: Jul. 11, 1997

[30] Foreign Application Priority Data

Jul. 12, 1996 [DE] Germany ................ 196 28 263.2

[51] Int. Cl.$^6$ ................ C08B 3/00; D01F 1/00; C12S 13/00
[52] U.S. Cl. ................ 536/56; 536/58; 252/364
[58] Field of Search ................ 536/56, 58; 252/364

[56] References Cited

U.S. PATENT DOCUMENTS 4,742,005  5/1988  Yamanobe et al. ................ 435/99

FOREIGN PATENT DOCUMENTS 44 39 149 A1  5/1996  Germany.

OTHER PUBLICATIONS

Organic solvent pretreatment to enhance enzymic saccharification of straw, Chemical Abstracts, vol. 109, p. 526, Aug. 1, 1988.

Making fibers, foils and other products from dissolved cellulose, Chemical Abstracts, vol. 125, p. 191, Oct. 14, 1996.

*Primary Examiner*—Nathan M. Nutter
*Attorney, Agent, or Firm*—Barnes & Thornburg

[57] ABSTRACT

The invention relates to a method of manufacturing cellulose solutions whereby cellulose is dispersed in an aqueous amino oxide solution and is treated with xylanase or enzyme mixtures containing xylanase.

12 Claims, No Drawings

METHOD OF MANUFACTURING CELLULOSE SOLUTIONS IN AQUEOUS AMINO OXIDE

The invention relates to a method of manufacturing cellulose solutions in aqueous amino oxide.

In the manufacture of fibres, foils and other shapes or objects from cellulose using the amino oxide process, what is so far known is to dissolve cellulose in certain aqueous tertiary amino oxides under heat. The procedure is usually that cellulose is dispersed in aqueous amino oxide solution and when it is heated in the vacuum, excess water is vaporized out of this dispersion, resulting in the dissolution of the cellulose. This solution is then pressed through nozzles and, after passing through an air gap in a precipitating agent which is frequently an aqueous amino oxide solution, coagulates.

Problems arise here in that both the amino oxide and the cellulose dissolved therein may be thermally damaged under the influence of the increased temperature at the correspondingly necessary sojourn time. For this reason and also for the reason of an accelerated throughput, the cellulose is to be brought very quickly and completely into solution with the aqueous amino oxide.

Different proposals have already been made for this. For example, in WO 95/11261 it is proposed that a suspension of cellulose in aqueous amino oxide solution should be subjected to high-consistency grinding and the dissolution process carried out subsequently.

Another possible way of improving the properties of the cellulose in relation to its solubility in aqueous amino oxide solution can be seen from EP 0 356 419. According to it, the cellulose should be ground dry, but this, however, where optimal grinding conditions are deviated from, leads to keratinization of the cellulose resulting from the thermal stress and this has a negative influence on the solubility of the cellulose. Alkalization with subsequent regeneration or hydrothermal treatment of the cellulose to improve the solubility of the cellulose is proposed by E. Taeger, CH. Michels and A. Nechwatal in "Das Papier" 45(1991) 784–788 or in DD 298 789. However, additional process steps are necessary for this and these considerably increase the expense.

It is also known that enzymes are only effective in a specific temperature and $p_H$ range and become inactive in the presence of specific foreign substances especially in the region of increased concentration [Brockhaus ABC Chemie in zwei Banden, VEB F. A. Brockhaus Verlag, Leipzig 1965, Vol.1, page 400; Herder-Lexikon der Biochemie und Molekularbiologie, Spektrum Akad. Verlag, Heidelberg, Berlin Oxford 1995, Vol. 1, pages 424–425].

Proceeding from this, it is the purpose of the present invention to propose a new method of manufacturing cellulose solutions in aqueous amino oxide by means of which accelerated dissolution of the cellulose should be achieved without significant additional measures.

The purpose is fulfilled by the characteristic features of claim 1. Advantageous developments are characterised by the features of the secondary claims.

It is thus proposed, according to the invention, to disperse cellulose in aqueous amino oxide solutions and treat it with xylanases. Surprisingly, it was established in this process that the activity of the enzymes admittedly changes in dispersions of cellulose in aqueous solutions of N-methylmorpholine-N-oxide in comparison with dispersions of cellulose in water, but that, nevertheless, the properties of the cellulose are so altered by the enzyme treatment of the cellulose in the aqueous amino oxide solution that quicker dissolution of the cellulose in the aqueous amino oxides is achieved. Enzyme mixtures containing xylanase can also be used. The use of xylanase from Trichoderma viride is especially preferred.

The production of the solution is modified according to the invention in such a way that xylanase or enzyme mixtures containing xylanase are added before, during or after dispersion of the cellulose in the aqueous amino oxide solution. After a sojourn time necessary for the enzyme to become effective, the excess water is removed by heating in a vacuum, the enzyme being destroyed and the cellulose dissolving. The enzyme can also be added to the aqueous amino oxide solution before the addition of the cellulose.

The possible treatment temperature in the enzyme reaction depends on the type of enzyme and with normal xylanases should lie between ambient temperature and 60° C. The necessary treatment time depends on the chosen enzyme concentration and the treatment temperature as well as on the concentration of the amino oxide solution. It has also proved to be advantageous if the cellulose concentration in the amino oxide solution containing the enzyme is more than 3%, preferably 5% to 15%. The enzyme activity in the dispersion should here be above 0.1 U/g. Particularly favourable results are achieved if these process parameters are adhered to.

The procedure according to the invention is to be explained in greater detail below by means of examples:

EXAMPLE 1

15.75 g prehydrolysis sulphate cellulose (corresponding to 15 g abs. dry cellulose) were dispersed in 195.68 g 60% aqueous solution of N-methylmorpholine-N-oxide and mixed with such a quantity of xylanase (from Trichoderma viride) that an activity of 4.35 U/g amino oxide solution was achieved. The dispersion was homogenized again and kept for 23 hours at 22° C. Then, with the addition of 0.15 g propyl gallate, the NMMNO content was first concentrated to 80% at 80° in a kneading device. 70 g of this slurry was further treated for 60 minutes at 70° C. in a metering kneading device. Then the temperature was raised to 95° C. and, once this temperature had been reached through the creation of a vacuum the water content was lowered to the NMMNO monohydrate value within 5 minutes and the dissolution process thereby initiated. Tracking the torque change and examining the samples in a polarizing microscope resulted in an evaluation of the dissolution process. The cellulose treated with the enzyme was completely dissolved after 12 minutes, whilst in a dissolution experiment carried out under the same conditions without the addition of any enzyme, dissolution was only achieved after 14 minutes.

EXAMPLE 2

In the production of the cellulose-amino oxide-water solution corresponding to the procedure of example 1, the dispersion of the cellulose in 60% aqueous amino oxide solution was mixed with such a quantity of xylanase that an activity of 5.8 U/g amino oxide solution was achieved. The mix was kept for 26 hours at 22° C. In the dissolution stage, the dissolution process was finished after 7.5 minutes.

EXAMPLE 3

In the production of the cellulose-amino oxide-water solution corresponding to the procedure of example 1, the dispersion of the cellulose in 60% aqueous amino oxide solution was mixed with such a quantity of xylanase that an activity of 7.25 U/g amino oxide solution was achieved. The mix was kept for 26 hours at 22° C. In the dissolution stage, the dissolution process was finished after 10 minutes.

EXAMPLE 4

In the production of the cellulose-amino oxide-water solution corresponding to the procedure of example 1, the dispersion of the cellulose in 60% aqueous amino oxide solution was mixed with such a quantity of xylanase that an activity of 5.8 U/g amino oxide solution was achieved. The mix was kept for 2 hours at 40° C. In the dissolution stage, the dissolution process was finished after 8.5 minutes.

EXAMPLE 5

In the production of the cellulose-amino oxide-water solution corresponding to the procedure of example 1, the dispersion of the cellulose in 60% aqueous amino oxide solution was mixed with such a quantity of xylanase (from Trichoderma viride) and cellulase (from Aspergillus niger) such that 5 U xylanase activity and 2 U cellulase activity/g amino oxide solution were achieved. The mix was kept for 24 hours at 22° C. In the dissolution stage, the dissolution process was finished after 10.5 minutes.

We claim:

1. Method of manufacturing celluose solutions, characterized in that cellulose is dispersed in an aqueous amino oxide solution and is treated with xylanase or enzyme mixes containing xylanase.

2. Method according to claim 1 characterized in that the enzyme treatment is carried out at temperatures between 20° C. and 60° C.

3. Method according to claim 1, characterized in that the cellulose concentration in the amino oxide solution containing the enzyme lies between 5% and 15%.

4. Method according to claim 1, characterized in that the enzyme activity in the dispersion is adjusted to be above 0.1 U/g.

5. Method according to claim 4, characterized in that xylanase from Trichoderma viride is used.

6. Method according to claim 2, characterized in that the cellulose concentration in the amino oxide solution containing the enzyme lies between 5% and 15%.

7. Method according to claim 2, characterized in that the enzyme activity in the dispersion is adjusted to be above 0.1 U/g.

8. Method according to claim 3, characterized in that the enzyme activity in the dispersion is adjusted to be above 0.1 U/g.

9. Method according to claim 6, characterized in that the enzyme activity in the dispersion is adjusted to be above 0.1 U/g.

10. Method according to claim 7, characterized in that xylanase from Trichoderma viride is used.

11. Method according to claim 8, characterized in that xylanase from Trichoderma viride is used.

12. Method according to claim 9, characterized in that xylanase from Trichoderma viride is used.

* * * * *